United States Patent [19]

Usher

[11] Patent Number: 4,784,986

[45] Date of Patent: Nov. 15, 1988

[54] SKIN TREATMENT COMPOSITIONS AND METHOD OF USE THEREOF

[75] Inventor: Thomas C. Usher, Nassau, The Bahamas

[73] Assignee: Polydex Pharmaceuticals Ltd., Nassau, The Bahamas

[21] Appl. No.: 925,061

[22] Filed: Oct. 30, 1986

[51] Int. Cl.$^4$ .......................... C08L 89/06; A61K 7/28
[52] U.S. Cl. .......................................... 514/2; 514/21; 514/801; 530/356; 424/101
[58] Field of Search ............................. 514/2, 21, 801; 530/356; 424/101

[56] References Cited

U.S. PATENT DOCUMENTS 3,898,129  8/1975  Fujimoto et al. .................. 530/356
4,485,037  11/1984  Curtis .................................... 424/61

Primary Examiner—Morton Foelak
Assistant Examiner—Nathan M. Nutter
Attorney, Agent, or Firm—I. Louis Wolk

[57] ABSTRACT

Cosmetic preparations comprising water soluble fatty acid amide derivatives of hydrolyzed collagen are found to have a substantial degree of permeability to the stratum corneum of human skin and to be effective in improving skin texture, moisture retention and minimizing wrinkles.

5 Claims, No Drawings

SKIN TREATMENT COMPOSITIONS AND METHOD OF USE THEREOF

BACKGROUND OF THE INVENTION

The skin consists of a number of overlapping layers of cells. The outermost layer of the skin is called the stratum corneum and consists of dead keratinized cells. This layer protects the skin from physical and atmospheric harm, acting as a barrier to external dangers. The stratum corneum, compared with the lower layers of the epidermis, is rather dry. Lack of moisture in the lower layers of the skin results in a wrinkled and aged look. Lack of moisture in the strateum corneum, however, is even more noticeable in that this is the layer that we see. The dryness is marked by roughness, increased flakiness, and in more severe cases, cracks and actual peeling. The skin may appear reddened and even inflamed if the dryness is sufficiently acute. It has been shown, by at least one scientist, that the stratum corneum remains soft and pliable only as long as the moisture content exceeds 10%. Below this, the skin becomes hard and brittle and develops an opacity.

In the lower layers of the skin, degenerative changes occur with age whereby not only moisture is lacking, but also a major amount of lipoidal or fatty substances. In cosmetic practice, it is the outermost layer of the skin which can best be benefitted by application of external lotions and creams. If this outermost layer can be made to look plump, transparent and healthy, the overall skin texture will assume a more youthful appearance, however, studies of the epidermis indicate that the stratum corneum is capable of absorbing and retaining only moisture. It will not accept lipid or fatty substances. Such materials used for moisturization of the skin have no direct effect whatsoever in increasing the hydration of the epidermal cells.

As the result of aging, exposure to various climatic conditions, such as, sun and wind and other factors in addition to loss of moisture in the epidermal layers of the skin, it has been found that loss of elasticity and skin tone and texture may occur through degradation of certain complex polypeptides present in the skin such as elastin and collagen, among others.

The collagens, a family of closely related proteins, are the main fibrillar components of the connective tissues and the major extracellular proteins of the human body. Examination of collagen in connective tissues by light microscopy demonstrates that collagen is deposited as large bundles of regularly oriented fibers which on further examination can be shown to be composed of fibrils and microfibrils. The microfibrils are aligned in a parallel manner which results in a pattern of cross-striations or bands which can be visualized by electron microscopy. The most prominent cross-striations appear as repeating bands which are spaced approximately 70 nm apart.

The basic collagen molecule has an approximate molecular weight of 290,000, and it is composed of three polypeptide chains, each having a molecular weight of about 94,000. These three polypeptides, so-called a chain, are coiled on each other much like strands of rope, so that the collagen molecule has a triple-helical structure. This unusual helical conformation gives the molecule a rigid, rodlike shape with approximate dimensions of $1.5 \times 300$ nm.

Despite the high molecular weight of native collagen and their high degree of insolubility, they may be degraded and solubilized by various procedures including acid and alkali treatment and subjection to enzymatic processes. Such procedures are described in numerous prior art patents and publications, among which for example, attention may be directed to U.S. Pat. Nos. 3,475,404, 3,548,056 and 4,140,537, and the publication of Todd and Biol, "Soluble Collagen—New Protein for Cosmetics" D & CI (Drug and Cosmetic Industry), October, 1975, pp. 50–56 and 134–138.

It has been stated that one of the characteristic features of collagen is that under physiologic conditions collagen molecules spontaneously assemble into insoluble fibers. This observation previously presented a problem in that it was difficult to visualize how a collagen molecule could be synthesized inside the cell and then secreted into the extracellular space without the molecules prematurely assembling into insoluble fibers. This question has now been answered by the demonstration that collagen is initially synthesized as a larger precursor molecule, pro-collagen, which is soluble under physiologic conditions. (Dermatology in General Medicine, Fitzpatrick et al, McGraw - Hill 1979, Chapter 5, page 166).

As referred to in the Todd and Biol publication referred to above, it has been suggested that "a feature of ageing is the progressive insolubilization of collagen through cross-linking and aggregation to produce a form of the protein more resistant to chemical attack, less able to retain moisture and more rigid in structure. The most obvious manifestation of these changes is the development of dry, wrinkled skin that has lost its inherent elasticity. One piece of evidence used to substantiate this theory is the frequent observation that the ratio of soluble to insoluble collagen is greater in young than in older animals—as demonstrated by the greater proportion of the total collagen of skin that is readily extracted."

It has also been suggested that cosmetic application of soluble collagen preparations supplies the skin with soluble collagen and induces formation of new fibrils, thus arresting the loss of natural soluble collagen and compensating for its loss.

The Todd and Biol publication further points out, however, that it is also difficult to visualize how soluble collagen cosmetic treatment could lead to absorption of soluble collagen for fibrillogenesis. "The molecular parameters of the tropocollagen macromolecule in solution have been deduced as about 3000A by 16A with a weight average molecular weight of about 300,000 and this alone must preclude skin penetration and absorption of the protein in an undenatured state."

It is suggested that the major function of soluble collagen in cosmetic preparations is as a highly efficient natural agent for the retention and enhancement of skin moisture.

The foregoing observations would appear to indicate that lower molecular weight collagens obtained by degradation or hydrolysis by native collagens may have some superficial activity in application to the skin.

Studies indicate that the stratum corneum is capable of absorbing and retaining only moisture and that it will not accept lipid or fatty substances. Further, when lipids are removed from the skin but water soluble substances are left in the skin, its ability to hold moisture is impaired. Accordingly, various preparations have been proposed which attempt to restore lipids to the surface of the skin accompanied by hygroscopic materials which attract and hold moisture. The preparations may include soluble collagens to improve surface texture of the skin as long as they remain applied to the surface thereof. Such formulations do not permit any significant penetration of the skin beyond the outermost layers thereof and therefore permit only transitory surface effects. Examples of such formulations are described in U.S. Pat. Nos: 3,548,056 and 4,454,159.

In the study of the structure of the stratum corneum, the dermatologists have used strips of plastic adhesive tape, such as, the well-known "Scotch" brand tape to remove successive layers of the stratum corneum with each piece of tape. This has been verified by staining of the cells removed by each layer followed by histological examination. For most individuals, the stratum corneum comprises aabout 12–18 layers of cells (sometimes considered as 10–20 layers). After this number of layers have been stripped from the same site of stratum corneum, there appears what is known as the "glistening layer" of the epidermis, which is so-called because at this layer tissue fluid starts to ooze out of the living cells.

It is believed that stripping off these layers of the stratum corneum followed by subsequent analyses of single or multiple layers gives a good indication of the degree of permeability of a material into the skin.

SUMMARY OF THE INVENTION

It has been found in accordance with the present invention that solubilized collagen materials which are water soluble can be reacted with a fatty acid moiety such as palmitic, oleic, or lauric acid to produce a complex which is also water soluble and which when applied to human skin permits a substantially enhanced degree of penetration through the first 12 layers of the stratum corneum as compared with corresponding underivatized collagens of the same or similar molecular weights.

At the same time it was found that similar fatty acid derivatives of higher molecular weight collagens which were water insoluble gave little or no improvement in penetrability in comparison with the collagens themselves. Thus, the dramatic improvement in degree of skin penetration must be attributed to the discovery that only the fatty acid derivatives of collagens which are water soluble would have this attribute.

When the collagen-fatty acid complex of this invention is incorporated in various cosmetic formulations of the prior art in place of collagen as heretofore utilized, significant improvements in skin texture with longer lasting effects are obtained. Such effects include not only improvement in texture and softness but also skin moisturizing and elimination or minimizing of small wrinkles.

In the development of the present invention it was first determined that hydrolysed collagens regardless of their molecular weight, themselves had almost no permeability beyond the first and second layers of the stratum corneum. In order to improve the degree of penetration, it was decided to determine whether the addition of a suitable alkyl group to an N-terminal group of the collagen molecule would accomplish this. Accordingly, it was decided to attempt the attachment of a fatty acid moiety such as lauric, palmitic or oleic acid.

The alkylation procedure was carried out by first converting the fatty acid to the corresponding anyhydride or chloride and then alkylating the collagen in aqueous solution to obtain collagen fatty acid derivatives in the form of the corresponding amides or fatty acid N-acyl derivatives, such as the laurate, oleate or palmitate or mixtures thereof as desired. The resulting products were then tested for skin permeability in comparison with underivatized collagens by tritiating the test substances, applying them to skin surfaces, removing successive layers of skin and measuring the radioactive absorption in such layers by means of liquid scintillation spectrocopy as described in the examples herein. As the test results demonstrate, while tritiated hydrolysed collagens showed little or no permeability to layers of the stratum corneum below the surface, the corresponding water soluble fatty acid derivatives showed a much higher degree of penetration in the lower layers of the stratum corneum as described in greater detail below.

When the derivatized collagens are incorporated in cosmetic preparations such as skin creams and utilized upon the skin for various periods of time, noticeable moisturizing and skin toning effects are obtained. In addition, it was found that wrinkles were often reduced or eliminated as evidence that the deep absorption of collagen was effective.

By contrast, when the same tests were carried out with underivatized water soluble collagens, no absorption was observed, or was greatly below that obtained with derivatives of water soluble collagens of the type described.

Thus, by the use of this technique, the degree of penetration of derivatized and underivatized collagens which have been radioactively tagged can be readily determined by means of liquid scintillation spectroscopy in a spectrometer designed for such use.

A liquid scintillation spectrometer is an instrument capable of measuring radioactive emissions within certain energy ranges. The sample is placed in an organic liquid medium containing a solute referred to as "flour". The flour, upon being contacted with a radioactive emission, usually a beta particle, is excited and subsequently decays with the emission of a photon. The photon is detected by a photocell and electronically counted. Therefore, the number of protons emitted per minute is related to the number of radioactive emissions per minute and this consequently may be referred to as the specific activity of the sample. The organic samples are encased in small glass vials called liquid scintillation counting vials. These are then appropriately placed in a Beckman liquid scintillation spectrometer and the analysis is carried out.

Tritium ($^3H$) is a weak beta emitter and is very suitable for liquid scintillation spectrometric analysis. Quenching of photoemission seems to occur with stripped skin samples and the counts analyzed may be slightly lower than the actual number of counts present. Quenching is possible to correct for but was not in the experiments reported here and is not thought to be a vital component of the present experiments.

As described further herein, experiments with low molecular weight collagen fractions and fatty acid derivatives thereof which had been "tagged" with tritium demonstrated the increased degree of penetrability achieved by the acyl derivatives described.

DETAILED DESCRIPTION OF THE INVENTION

Alkylation of the collagens was carried out by reacting the anhydride or chlorides of a fatty acid, such as lauric, oleic or palmitic or mixtures thereof, with the collagen in aqueous solution and recovering the acylated collagen product.

These products were then tested and utilized in various skin formulations as described below. Corresponding products which had been "tagged" with tritium were tested against the collagens themselves, also so tagged for comparison of skin permeability as described in the following examples.

EXAMPLE I

Preparaton of fatty acid amides of soluble collagens.

For the preparation of the lauric acid amide of soluble collagen by reaction with lauroyl chloride: 200 ml of an aqueous solution of soluble hydrolysed collagen (3%) was reacted with 40 ml of a 3.5% solution of lauroyl chloride in acetone added dropwise and adjusted to a pH of 8 with stirring at a temperature of 24° C. The reaction mixture was stirred over night and the reaction product was separated by centrifuging in the form of a creamy white precipitate. Other fatty acid amides are prepared in similar manner.

For the preparation of the fatty acid amine by reaction of collagen with the anhydrides of fatty acids, the anhydrides may be obtained from commercial sources or prepared in known manner by reaction with thionyl chloride in tetrahydrofuran pyridine solution and recovery of the anhydride from the solution.

For the preparation of the lauric acid amide 100 ml of aqueous solution of hydrolized collagen (10%) are reacted with 1.5 grams of lauryl anhydride in acetone solution added dropivise while stirring at 40° C. for 1 hour. The reaction is allowed to continue for 14 hours with stirring at that temperature. At the end of this time, the reaction mixture is twice extracted with 50± volume of chloroform to remove unreacted fatty acid and the aqueous reaction mixture dialysed to further remove unreacted lauric acid and lauric anhydride. The final solution may be concentrated to recover the solid fatty acid amide or the final solution adjusted to a desired concentration for testing or use in cosmetic preparation.

For testing of this product for permeability upon human skin, collagen is reacted with tritiated lauroyl chloride or lauric anhydride in the preparation of the correspondign tritiated fatty acid amide. This is generally accomplished by reaction with tritiated acetic anhydride in known manner.

EXAMPLE II 100 mg. of small molecular weight soluble hydrolysed collagen, m.w. 2800, was treated with tritiated acetic anhydride having a total number count of $50 \times 10^8$ counts per minute. Both the collagen and the triated acetic anhydride were obtained from commercial laboratories. The reactants were rapidly stirred in a reaction vessel with 10 ml of ether and 2 ml of water under reflux conditions for 48 hours. The product was then purified by exclusion chromatography and found to have a radioactivity of approximately 1275 per minute per milligram of solid material. This was diluted to a 10% solution in water which contained 127 counts per microliter of solution.

Two experiments were then carried out. First, 5 microliters of product was added to one square centimeter of human forearm for an exposure of 1 hour. Next, 5 microliters of material was added to one square centimeter of the same human forearm for a period of two hours. At the end of each period, 12 cellophane or "Scotch" tape strippings of successive layers were taken and tested in a Beckman liquid Scintillation Spectrometer in order to analyse the counts absorbed and retained by the various layers as in indication of the penetration of the collagen material.

The following results were obtained:

| Layers | Counts | % | Recovered/ug |
|---|---|---|---|
| (a) 1 HOUR TEST | | | |
| 1-2 | 285 | 96 | 156 |
| 3-9 | 15 | 4 | 3.1 |
| 10-12 | 0 | 0 | 0 |
| (b) 2 HOUR TEST | | | |
| 1-2 | 281 | 91 | 220 |
| 3-9 | 23 | 7 | 18 |
| 10-12 | 5 | 1 | 4 |

These results show only a trivial degree of penetration into the lower layers of the stratum corneum after a two hour exposure.

EXAMPLE III

Hydrolysed soluble collagen, m.w. 2800 which had been derivatized with lauric acid in the manner described above to form the corresponding amide was trivially trans-acetylated with tritiated acetic anhydrid and was used for a penetration experiment on human skin.

Five milligrams of the derivative was applied to 1 sq. centimeter of human forearm. The product had a radioactivity of 575 counts per minute. Two experiments were carried out in this manner. One was for an exposure time of 1 hour followed by 12 cellophane tape strippings of the skin and one was with a 2 hour exposure also followed by 12 tape strippings. The data which resulted are shown in the tables below.

| Layers | Counts | % distribution | Recovered/ug |
|---|---|---|---|
| TAPE STRIPPING OF EPIDERMIS (1 Hour) | | | |
| 1-2 | 120 | 54 | 104 |
| 3-9 | 88 | 40 | 35 |
| 10-12 | 15 | 7 | 6 |
| TAPE STRIPPING OF EPIDERMIS (2 Hours) | | | |
| 1-2 | 111 | 46 | 97 |
| 3-9 | 96 | 38 | 33 |
| 10-12 | 35 | 14 | 12 |

The above data show a significant degree of penetration beneath the outermost two layers of the skin particularly when compared with the results obtained with the nonderivatized collagen tests in Example II.

EXAMPLE IV

Skin measurement tests with mixed lauric and stearic acid amides of 1000 m.w. and 10,000 m.w. soluble collagens.

Lauroyl chloride was treated with radioactive stearic acid to allow acid chloride equilibration to occur by adding 5 millecuries to 2 mls. of lauroyl chloride and allowing to stand for 10 days.

50 mg. fractions of each molecular weight collagen were used to make radioactive derivatives by reacting with fractions of the radioactive mixed fatty acids as described above in Example I.

Skin measurements were carried out on the 1000 m.w. and 10,000 m.w. fractions as described above in Examples II and III on 1 square centimeter of forearm skin patches. The samples used were adjusted in specific activity to 20,000 counts per minute per milligram of the 1000 m.w. fraction and 2000 counts per milligram of the 10,000 m.w. fraction, with both samples being adjusted to 10% weight to volume in neutral pH water.

The data from these experiments is tabulated below. The test duration was 1 hour.

1000 m.w. fraction (1.1 mg)

| SKIN LAYER | COUNTS | % DISTRIBUTION | RECOVERED/Ug |
|---|---|---|---|
| 1-2 | 16.416 | 75 | 754 |
| 3-8 | 4,937 | 22 | 227 |
| 9-12 | 428 | 2 | 20 |
| 10,000 m.w. fraction (1 mg) | | | |
| 1-2 | 1438 | 86 | 856 |
| 3-8 | 223 | 13 | 133 |
| 9-12 | 19 | 1 | 11 |

The above data shows that both 1000 m.w. derivatives and the 10,000 m.w. derivatives have a significant degree of penetration but somewhat greater for the lower molecular weight product.

With respect to the tests with radioactive material, it may be noted that the number of counts applied to the skin is usually greater than the number of counts recovered. It is possible that some of the counts applied to the surface of the skin are low in various mechanical ways. It is also possible that some of the counts actually penetrate to a deeper depth than is pulled off by the tape strippings or that the skin causes a quenching of counts which cannot be picked up easily by the tape. However, such discrepancies are minor and the above data as set forth in the examples clearly indicates that the fatty acid collagen derivatives are effective in permeating the stratum corneum to add collagen content to the skin.

The water soluble fatty acid collagen amides described above may be formulated into conventional types of cosmetic creams or lotions for application to human skin. As desired, these materials may be applied per se to the skin directly or in aqueous solution or as the sole cosmetic constituent of such creams or lotions but as a matter of convenience in application and elegance of formulation are preferably admixed with conventional compounding ingredients such as fatty alcohols, petroleum jelly, triglycerides, emulsifying agents, fillers, perfumes and preservatives, etc.

Typical formulations in which the products of the invention may be incorporated are described below. Preferred proportions of the fatty acid collagen derivatives may range from 1-10% as required or desired.

EXAMPLE V

Emollient skin cream

| | Parts by Weight |
|---|---|
| Petroleum Jelly | 8.00 |
| Mineral Oil | 8.00 |
| White Beeswax | 10.00 |
| Lanolin | 6.00 |
| Water | 40.00 |
| Perfume | q.s. |
| Lauric acid amide of soluble collagen, m.w. 2800 | 2.00 |

The above product provides a soothing skin cream which when applied and allowed to remain on the skin for at least one hour allows the collagen derivative to penetrate deeply and result in noticeable improvement in skin texture. Continued use would alleviate drying, retard skin ageing, and minimize formation of wrinkles. This cream can function as a night cream in which effectiveness will be enhanced by allowing it to remain on the face or hands for long periods of time to ensure a greater degree of penetration. This would also apply to any cosmetic preparation containing the collagen fatty acid amide where long duration of retention is possible.

EXAMPLE VI

Skin lotion

| | % W/W |
|---|---|
| Isopropyl Myristate | 3.0 |
| Polyethylene Glycol 1000 Monostearate | 3.0 |
| Lanolin Alcohol | 1.5 |
| Mineral Oil | 4.0 |
| Ethyl Alcohol | 6.0 |
| Glycerine | 2.0 |
| Sodium Lauryl Sulfate | 0.5 |
| 5% Solution in distilled water of Lauric Acid Amide of Soluble Collagen m.w. 1000 | 80.0 |
| Perfume and Color | q.s. |

This lotion is typical of many such products in which the active ingredient may be replaced or supplemented by the collagen fatty acid derivatives described herein.

EXAMPLE VII

Skin lotion

| | Parts by Weight |
|---|---|
| Glycerine | 30 |
| Ethyl Alcohol | 10 |
| Mineral Oil | 2 |
| Lanolin | 2 |
| Sodium Lauryl Sulfate | 1 |
| Distilled water solution containing 5% of water soluble fatty acid amide of soluble hydrolysed collagen selected from lauric and oleic acid or palmitic acid or mixture thereof | 45 |

The components are thoroughly mixed to become emulsified and will provide a penetrating, moisturizing and skin softening effect when applied to the skin and allowed to penetrate.

As described above and verified by the experimental data described in I-IV, applicant has described his discovery that the ability to penetrate multiple layers of the stratum corneum can be imparted to water soluble hydrolysed collagen by reaction with fatty acids to form the corresponding N-acyl derivatives or amides. In this way the beneficial effects of collagen upon the skin can be greatly enhanced and at the same time, the incorporation of the fatty acid molecules can introduce lipid materials which would not otherwise penetrate into such layers.

I claim:

1. A cosmetic method for the treatment of skin by the deep absorption of a collagen derivative into the stratum corneum thereof which comprises applying to the skin an effective amount of a water soluble fatty acid amide of a water soluble hydrolysed collagen having a molecular weight in the range of about 1,000–10,000, and allowing said material to remain in contact with the skin for a sufficient period of time to effect substantial penetration thereof.

2. A method according to claim 1 wherein the said fatty acid amide is applied in the form of a lotion.

3. A method according to claim 1 where the said fatty acid amide is applied in the form of a cream.

4. A method according to claim 1 wherein said fatty acid amide is allowed to remain in contact with the skin for at least one hour in order to ensure deep penetration thereof beneath the surface layers of the stratum corneum.

5. A cosmetically acceptable composition for application to the skin which comprises a water soluble fatty acid amide of water soluble hydrolysed collagen having a molecular weight ranging between about 1000 and 10,000 capable of deep penetration of multiple layers of the stratum corneum of the skin.

* * * * *